United States Patent [19]

Cheng et al.

[11] Patent Number: 5,008,252

[45] Date of Patent: Apr. 16, 1991

[54] PROCESS FOR INHIBITING HERPES SIMPLEX VIRUS-SPECIFIED THYMIDINE KINASE

[75] Inventors: Yung-chi Cheng, Chapel Hill, N.C.; Miroslav Bobek, Williamsville, N.Y.

[73] Assignees: The University of North Carolina at Chapel Hill, Chapel Hill, N.C.; Health Research, Inc., Buffalo, N.Y.

[21] Appl. No.: 28,507

[22] Filed: Mar. 20, 1987

[51] Int. Cl.$^5$ .................... A61K 31/70; A61K 31/045
[52] U.S. Cl. .................................... 514/50; 514/729; 514/934
[58] Field of Search .................. 514/49, 50, 729, 934; 536/23

[56] References Cited

FOREIGN PATENT DOCUMENTS 2838644  9/1979  Fed. Rep. of Germany ........ 514/49
1331520  9/1973  United Kingdom ................ 514/729

OTHER PUBLICATIONS

Sharma et al., J. Org. Chem. 43, No. 2, pp. 367–369 (1978).

Nutter et al., the Chemical Abstracts 106:188509g (1987).

*Primary Examiner*—John W. Rollins
*Attorney, Agent, or Firm*—Cushman, Darby & Cushman

[57] ABSTRACT

The invention relates to a method of selectively inhibiting herpes simplex virus-specified thymidine kinase. The method comprises exposing mammalian cells infected with the virus to an effective amount of 5'-ethynylthymidine. The invention further relates to a pharmaceutical composition comprising 5'-ethynylthymidine as the active ingredient together with a pharmaceutically acceptable carrier.

14 Claims, 5 Drawing Sheets

PROCESS FOR INHIBITING HERPES SIMPLEX VIRUS-SPECIFIED THYMIDINE KINASE

BACKGROUND OF THE INVENTION

TECHNICAL FIELD

The present invention relates, in general, to the inhibition of thymidine kinase, and, in particular, to a method of inhibiting herpes simplex virus-specified thymidine kinase.

BACKGROUND INFORMATION

Herpes simplex viruses type-1 (HSV-1) and type-2 (HSV-2) and varicella-zoster virus induce unique virus-specified thymidine kinases (dThd kinase) in cells that they infect. In the past, major efforts have been made to develop antiviral compounds that would serve as "selective alternative substrates" for virus-specified dThd kinase. While the activity of viral dThd kinase does not appear to be critical for virus replication in cell culture systems, several studies indicate that the enzyme may be important for virus pathogenicity and for activation of latent virus in neural cells (Darby, G., Field, H. J., and Salisbury, S. A. (1981) Nature (London) 289:81–83; Field, H. J. and Darby, G. (1980) Antimicrob. Agents Chemother. 17:209–216; Tenser, R.B., Miller, R.L. and Rapp, F. (1979) Science 205:915–917). These findings indicate that a selective inhibitor of virus-specified dThd kinase would be useful in the prevention of reactivation of latent virus.

SUMMARY OF THE INVENTION

It is an object of the present invention to provide a method of selectively inhibiting HSV-specified dThd kinase in mammalian cells infected with HSV.

It is another object of the invention to provide a method of inhibiting HSV-specified dThd kinase that poses minimal mutagenic or carcinogenic risk to the host cell.

It is a further object of the invention to provide a method of decreasing the dThd 5'-triphosphate (dTTP) pool of mammalian cells infected with HSV.

Further objects and advantages of the present invention will be apparent from the following detailed description of species thereof.

The objects of the present invention are achieved by exposing mammalian cells infected with HSV to the dThd analogue, 5'-ethynylthymidine (5'-Et-dThd) in an amount sufficient to selectively inhibit the HSV-specified dThd kinase. The analogue inhibits both HSV-1- and HSV-2-specified dThd kinase as well as dThd kinase induced by virus variants. The analog does not exhibit inhibitory activity against human cytosolic dThd kinase and it is not phosphorylated by dThd kinase. The compound has the potential of preventing HSV reactivation, since viral dThd kinase may be critical for the reactivation of latent HSV.

BRIEF DESCRIPTION OF THE DRAWINGS

FIG. 1A shows the activity of 5'-Et-dThd against purified HSV-1 (KOS), HSV-2, (333) and human cytosolic dThd kinase at a concentration of 100 μm [$^{14}$C]dThd in the assay mixture (the 100% dThd kinase activity values for human cytosolic (□), HSV-1 (Δ), and HSV-2 (O) enzymes were 0.94, 2.3 and 2.1 nmoles/min/ml enzyme, respectively). FIG. 1B shows the effects of 5'-Et-dThd on intracellular dThd kinase activities of HSV-1 and HSV-2 infected HeLa BU cells and on mock infected HeLa S3 cells at 9 h post infection (the 100% dThd phosphorylation values for HeLa BU cells infected with HSV-1 (Δ) and HSV-2 (O) and mock infected HeLa S3 (□) cells were 33,000, 20,000 and 10,667 cpm/10$^6$ cells, respectively).

FIG. 2 The role of host dThd kinase in virus-infected cells. The effect of 5'-Et-dThd (25 μM) on intracellular dThd phosphorylation in HeLa S3 and HeLa BU cells was compared at 9 h post infection.

FIG. 3B: Effect of 5'-Et-dThd on dNTP pools in 9 h HSV-1 (KOS)-infected HeLa BU cells—the 100% values for dCTP (O) dGTP (Δ), dATP (X) and dTTP (●) pools in HSV-1-infected HeLa BU cells being 64, 65, 75 and 159 μM, respectively; impact of 5'-Et-dThd on dTTP pools of HSV-1 (strain MDK)-infected HeLa BU cells—the dTTP pool of MDK-infected (□) HeLa BU cells being 70 μM.

DETAILED DESCRIPTION OF THE INVENTION

Figure 1:
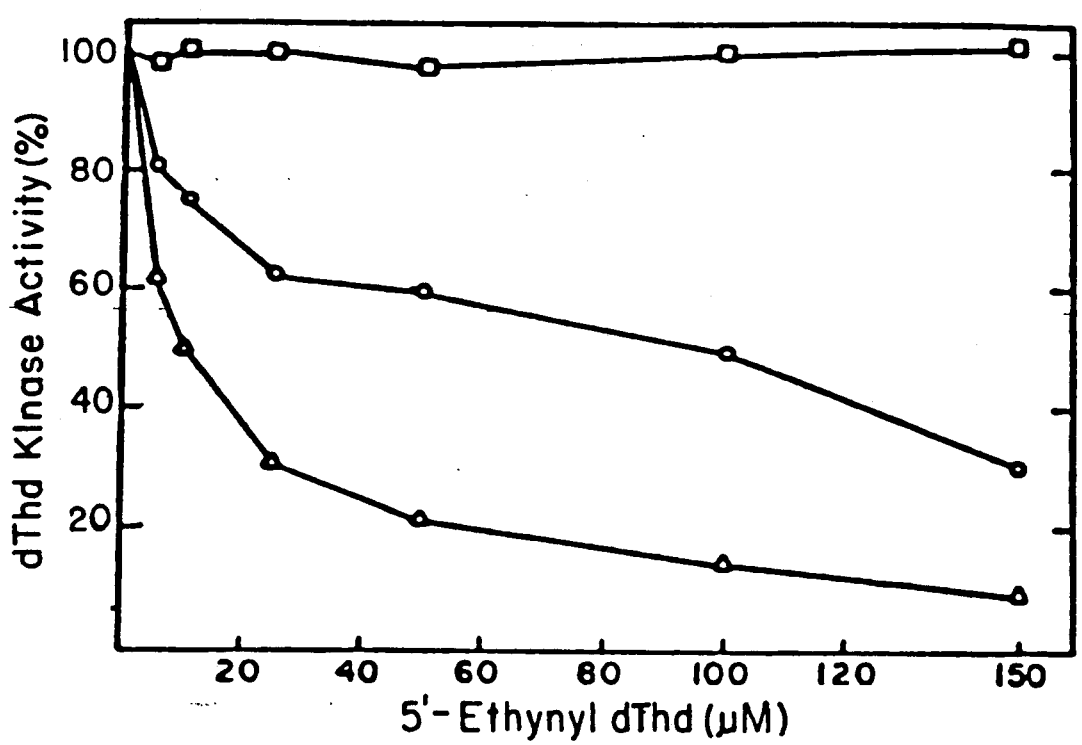
FIG. 1 Effect of 5'-Et-dThd on in vitro dThd kinase activity and intracellular dThd phosphorylation.
Figure 1:
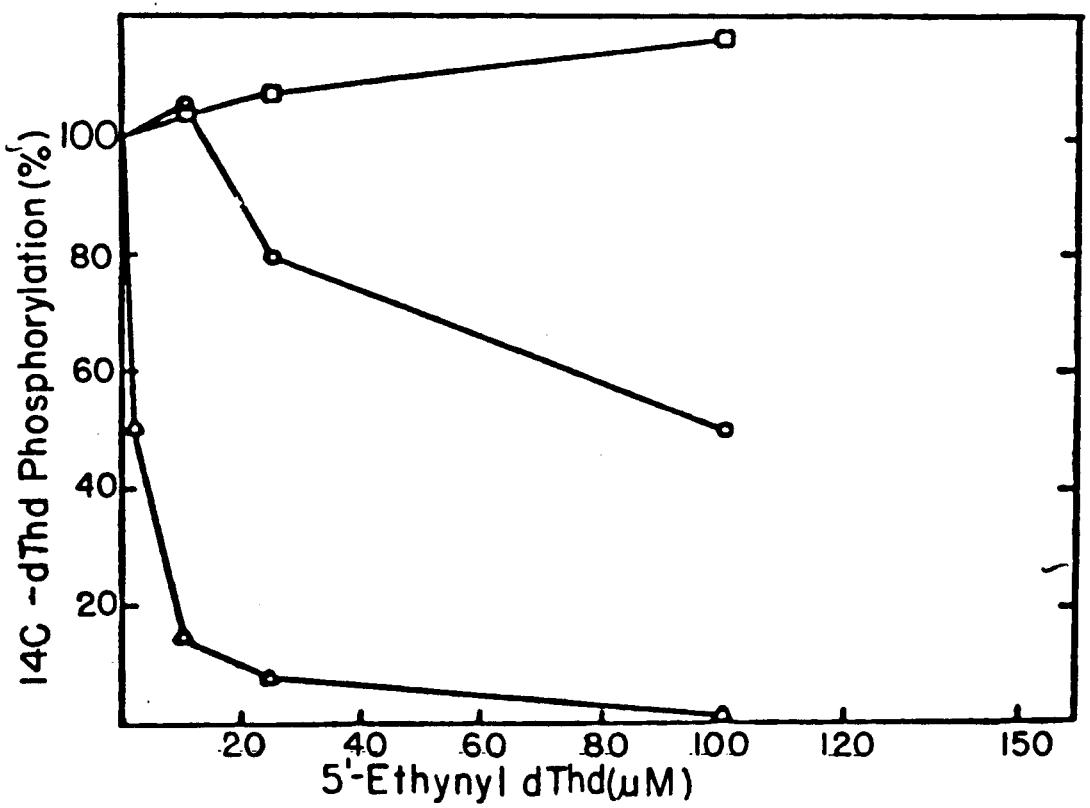

The invention contemplates the use of the dThd analogue, 5'-Et-dThd, as a selective inhibitor of HSV-specified dThd kinase. 5'-Et-dThd inhibits both HSV-1- and HSV-2-specified dThd kinase, particularly HSV-1. 5'-Et-dThd also inhibits dThd kinase induced by virus variants resistant to antiviral agents, such as acyclovir (ACV). The variant-specified dThd kinase (dThd kinase$^A$) displays a substrate specificity different from that of dThd kinase. Thus the invention relates to a method of inhibiting viral dThd kinase activity, whether of a wild-type or altered substrate phenotype. The invention also contemplates the use of 5'-Et-dThd as an inhibitor of the virus-specified dThd kinase produced by herpes zoster virus.

Both host and viral dThd kinase can utilize dThd as a substrate. HSV-infected dividing cells have higher levels of phosphorylated dThd nucleotides than virus-harboring, resting/non-dividing cells with diminished host dThd kinase activity. Therefore, dThd phosphorylation in the latter cell type is expected to be more susceptible to the effect of 5'-Et-dThd than is dThd phosphorylation in the former cell type. Accordingly, it is anticipated that 5'-Et-dThd would be particularly effective in inhibiting HSV-specified dThd kinase activity in infected neural cells.

5'-Et-dThd exhibits no effect against human cytosolic dThd kinase. In addition, the analog is not phosphorylated by viral dThd kinase and thus mutagenic effects caused by metabolism and subsequent incorporation of 5'-Et-dThd into cellular DNA are not anticipated. Furthermore, 5'-Et-dThd (100 μM) has no effect on mammalian host DNA synthesis as measured by $^{32}PO_4$ incorporation, nor does the analog inhibit mammalian cell growth.

5'-Et-dThd (100 μM) significantly decreases the dTTP pool of HSV-infected mammalian cells (dCTP, dATP and dGTP pools are not significantly affected by the analogue). Accordingly, the invention contemplates a method of enhancing the antiviral activity of viral dThd kinase-independent antiviral agents that compete with dTTP for viral polymerase. The method comprises exposing infected cells to effective amounts of both 5'-Et-dThd and an appropriate antiviral agent, for example, aphidicolin.

The invention further contemplates a pharmaceutical composition for use in inhibiting HSV-specified dThd kinase or herpes zoster virus-specified dThd kinase comprising 5'-Et-dThd as an active ingredient together with a pharmaceutically-acceptable solid or liquid carrier, diluent or excipient therefor. The composition contains an amount of 5'-Et-dThd sufficient to selectively inhibit HSV-specified dThd kinase or herpes zoster virus-specified dThd kinase present in mammalian cells infected with HSV or herpes zoster virus. ,The composition may take any of the conventional forms for effective administration, e.g. pills, tablets, sterile injectable solutions and the like. When the composition is administered internally, a preferred serum circulation level is 10–100μM. The composition may also take any of the conventional forms for topical application, e.g. creams, lotions and the like.

EXPERIMENTAL

5'-Ethynyl was synthesized according to known procedures (Sharma, R.A. & Bobek, M. (1978) J. Org. Chem. 43:367-369).

Cells. The cells used were HeLa S3, HeLa BU (dThd kinase deficient), Vero and KB6B (Domin, B.A., Grill, S.P. and Cheng, Y.-C. (1981) Proc. Am. Assoc. Cancer Res. 22:920). The cells were maintained at 37° C. in RPMI 1640 medium supplemented with 5% fetal bovine serum and 100 μg/ml kanamycin. All cultures were found to be mycoplasma free by the BRL Mycotect (McGarrity, G.J. & Carson, D.A. (1982) Exp. Cell Res. 139:199-206) and 4,6-diamidino-2-phenylindole fluorescence (Russell, W. C., Newman, C. & Williamson, D.H. (1975) Nature (London) 253:461–462) techniques.

Virus stocks. The viruses used were HSV-1 (strains KOS, SC16, B3 and Tr7) and HSV-2(strain 333). dThd kinase mutants of HSV (SC16), B3 and Tr7, were isolated in the presence of (E)-5-(2-bromovinyl)-2'-deoxyuridine (BVDU) at 10 μg/ml and ACV at 1 μg/ml, respectively (Darby, G., Field, H.J. & Salisbury, S. A. (1982) Nature (London) 289:81-83; Field, H.J & Neden J. (1982) Antiviral Res. 2:243254).

HSV-1 or HSV-2was added at a low multiplicity of infection (0.01 plaque-forming unit (PFU) per cell) to confluent Vero monolayers. After a 1 h adsorption period, 30 ml of RPMI 1640 medium supplemented with 2% fetal bovine serum were added. The cells were then incubated at 37° C. for 24 h followed by incubation at 34° C. for 48 h (HSV-1 ) or 24 h (HSV-2). At the end of the incubation period the cells were suspended and frozen at −70° C. Prior to usage, the virus stocks were sonicated with two 10 s bursts on a Branson Sonifier with a Cup Horn adapter to retain sterility. The suspension was centrifuged for 10 min at 3,000 rpm to remove the remaining cells. The medium containing virus was then aliquoted into sterile tubes and stored at −70° C.

Cell and virus growth inhibition. Cell growth inhibition and the virus yield assay were performed in accordance with the protocol described by Cheng, Y.-C., Grill, S.P., Ruth, J. and Bergstrom, D. E. (Antimicrob. Agents Chemother. 18:957–961 (1980)) with the exceptions that all studies were done using 5% dialyzed fetal bovine serum; the multiplicity of infection was 3 PFU/cell and Vero cells were used instead of CV-1 cells for titration in the virus yield assays.

dNTP pool assay. dNTP pool measurements were done as described by Williams, M. W., Chang, C. H. and Cheng, Y.-C. (J. Biomed. Biophys. Meth. 1:153–1 62 (1979)). 5'-Et-dThd alone had no effect on the dNTP pool assay.

Enzyme purification, enzyme assays, $IC_{50}$ and $K_i$ determinations. The cellular cytosolic dThd kinase used to determine the $K_i$ values was isolated from KB6B cells. The HSV-1 and HSV-2dThd kinases were extracted from dThd kinase-deficient HeLa BU cells infected with HSV-1 (strain KOS) and HSV-2(strain 333), respectively. All of the dThd kinases were purified using affinity column chromatography procedures described by Lee, L. S. and Cheng, Y.-C. (J. Biol. Chem. 251:2600–2604 (1976)). The dThd kinase assay used was the same as that described by Cheng, Y.-C. & Ostrander, M. (J. Biol. Chem. 251:2605-2610 (1976)). Incubations were conducted at 37° C. for 60 min and the $K_i$ and 50% infectious concentration ($IC_{50}$) values were determined as described by Cheng, Y.-C. and Prusoff, W. H. (Biochem. Pharmacol. 22:3099–3108 (1976)).

The thymidylate kinase and synthase assays were performed according to known procedures (see, Cheng, Y.-C. & Prusoff, W. H. (1974) Anal. Biochem. 60:545–550; Roberts, D. (1966) Biochemistry 5:3546–3548; Dolnick, B. J. & Cheng, Y. C. (1977) J. Biol. Chem. 252:7697–7703). dThd phosphorylase activity was determined by monitoring conversion of [$^{14}$C]dThd to [$_{14}$C] thymine using high performance liquid chromatography (HPLC). Briefly, after a 30 min incubation of enzyme extract with radiolabeled dThd at 37° C., the reaction was stopped by addition of 25% trichloroacetic acid. After neutralization and centrifugation, the supernatants were loaded on to an Alltech Lichrosorb RP-18 column, and the column was eluted at a rate of 1 ml/min with 5 mM $KH_2PO_4$(pH 3.5)—10% methanol. Fractions of 1 ml were collected and radioactivity associated with dThd and thymine (as previously determined by retention times of authentic markers measured by their absorbance at 265 nM) was measured by scintillation counting. For evaluation of whether 5'-Et-dThd could serve substrate for dThd phosphorylase, reactions were carried out as described as above, except that 5'-Et-dThd was used instead of [$^{14}$C]dThd; metabolites were then analyzed by HPLC as described above.

Intracellular dThd kinase activity. HeLa S3 or HeLa BU cells ($1.5 \times 10^6$/ml) were mock infected or infected with HSV-1 or HSV-2at 3 PFU/cell and incubated at 37° C. for a 1 h adsorption period. The medium was then removed, and the cells were washed with growth medium and resuspended at a cell density of $5 \times 10^5$ cells/ml in RPMI 1640 medium supplemented with kanamycin (100 μg/ml) and 5% dialyzed fetal bovine serum. At 9 h post-HSV infection, [14C]dThd (0.16 μCi/ml; 1 μM dThd) and different amounts of 5'-Et-dThd were added to the medium depending on experimental conditions. At the end of the labeling period (1 h), the cells were pelleted by centrifugation, washed with phosphate-buffered-saline (PBS) and resuspended in a small volume of PBS. Aliquots were then pipetted directly onto DE81 discs which were immediately washed in 100% EtOH. The DE81 discs were washed two additional times in 100% EtOH, and then radioactivity associated with the discs was measured by scintillation counting in 5 ml of aqueous counting fluid. In this manner, total intracellular dThd kinase activity was determined from the sum of radioactive acid soluble dThd nucleotides plus the acid insoluble dTMP associated with DNA, both precipitated directly on the DE81 discs.

The invention is illustrated by way of the following non-limiting examples:

EXAMPLE 1

Activity of 5'-Et-dThd against viral and cellular dThd kinase activities in vitro and in cell culture HSV-1- and HSV-2-induced dThd kinases that are different from those of their host cellular counterparts (see Cheng, Y.-C. (1976) Biochem. Biophys. Acta 452:370–381) were examined for their sensitivity to 5'-Et-dThd. The activity of 5'-Et-dThd against purified HSV-1 (KOS), HSV-2(333) and human cytosolic dThd kinase at a concentration of 100 μM [$^{14}$C]dThd in the assay mixture is shown in FIG. 1A (the 100% dThd kinase activity values for human cytosolic (□), HSV-1 (Δ), and HSV-2(0) enzymes were 0.94, 2.3 and 2.1 nmoles/min/ml enzyme, respectively). At 10 μM, 5'-Et-dThd inhibited 50% and 25% of HSV-1 and HSV-2 dThd kinase activities, respectively. Furthermore, 5'-Et-dThd was a potent inhibitor of HSV-1 (strain KOS) dThd kinase-associated dTMP kinase activity with IC$_{50}$ values of 0.3 μM and 0.8 μM when dTMP substrate concentrations of 25 μM and 100 μM, respectively, were employed in the assay (see Table I). No demonstrable effects on purified human cytosolic dThd kinase were observed when concentrations of 5'-Et-dThd as high as 150 μM were employed under identical assay conditions (FIG. 1A). Results from kinetic studies showed that 5'-Et-dThd was a competitive inhibitor with respect to dThd, and K$_i$ values were estimated to be 0.09 μM and 0.38 μM for HSV-1 (strain KOS) and HSV-2(strain 333) dThd kinase, respectively (see Table I). 5'-Et-dThd did not serve as a substrate for virus dThd kinase as determined by the phosphate transfer assay using dThd kinase from HSV-1 (KOS)-infected HeLa BU cells as an enzyme source and 2 mM ATP (see Doberson, M. J., and Greer, S. (1975) Anal. Biochem. 67:602–610).

The effects of 5'-Et-dThd on intracellular dThd kinase activities of HSV-1 and HSV-2 infected HeLa BU cells and on mock infected HeLa S3 cells at 9 h post infection were examined (see FIG. 1B; the 100% dThd phosphorylation values for HeLa BU cells infected with HSV-1 (□) and HSV-2(O) and mock infected HeLa S3 (□) cells were 33,000, 20,000 and 10,667 cells, respectively). At 100 μM, 5'-Et-dThd Et-dThd inhibited 97% of HSV-1 dThd kinase-mediated [$^{14}$C]dThd phosphorylation, and 50% of that mediated by HSV-2 dThd kinase in HSV-2 infected HeLa BU cells. The accumulation of intracellular phosphorylated [$^{14}$C]-dThd metabolites was increased slightly in mock-infected HeLa S3 cells treated with increasing amounts of 5'-Et-dThd (FIG. 1B).

Figure 2A:
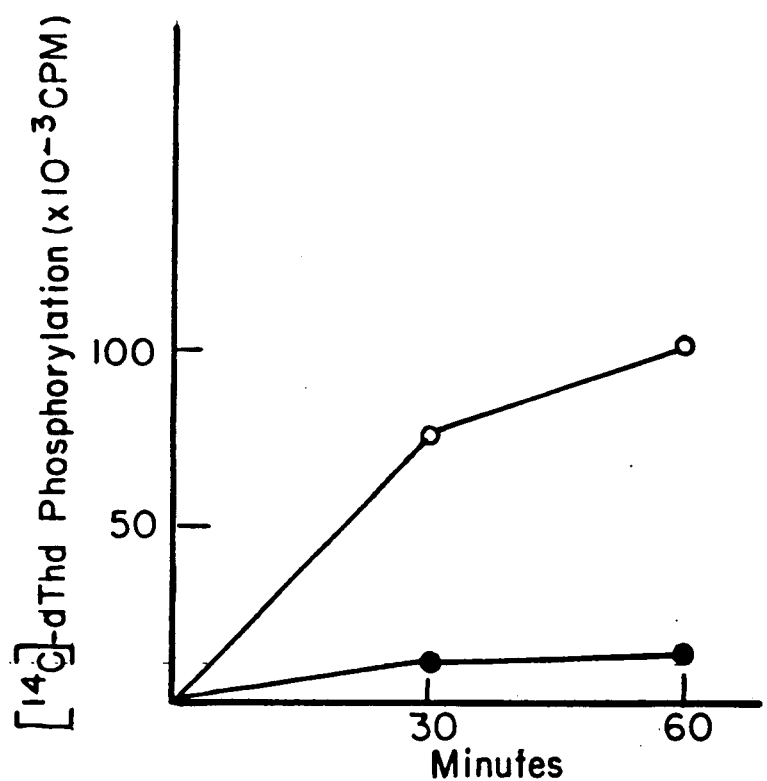
FIGS. 2A and 2B show the percent of the untreated control dThd phosphorylating activities present in HeLa BU cells infected with HSV-1 and HSV-2 (phosphorylation in the absence (O) or presence (●) of 25 μM 5'-Et-dThd)
Figure 2B:
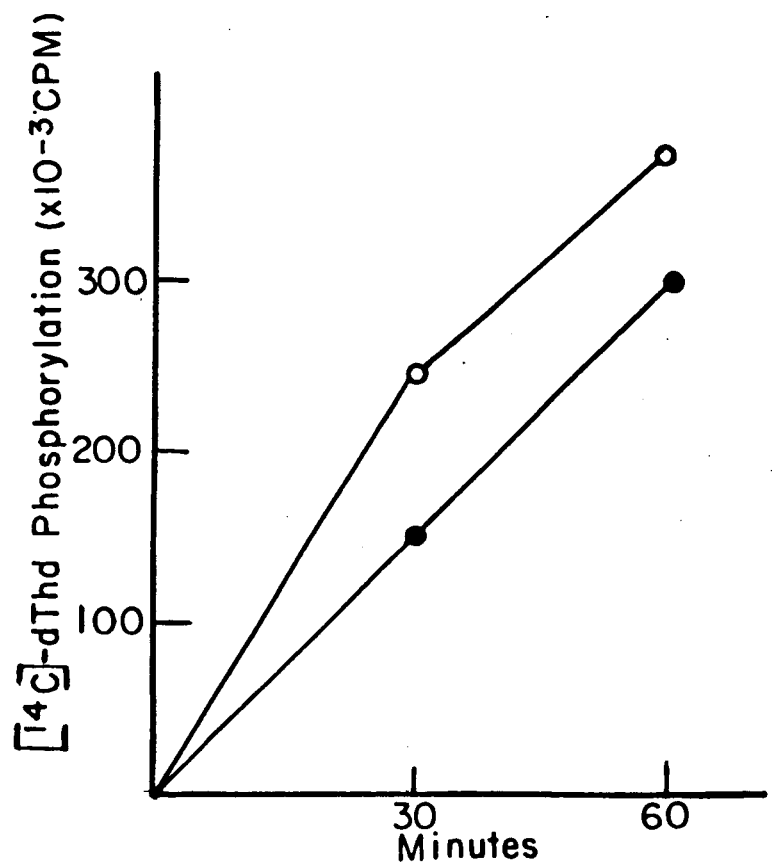
Figure 2C:
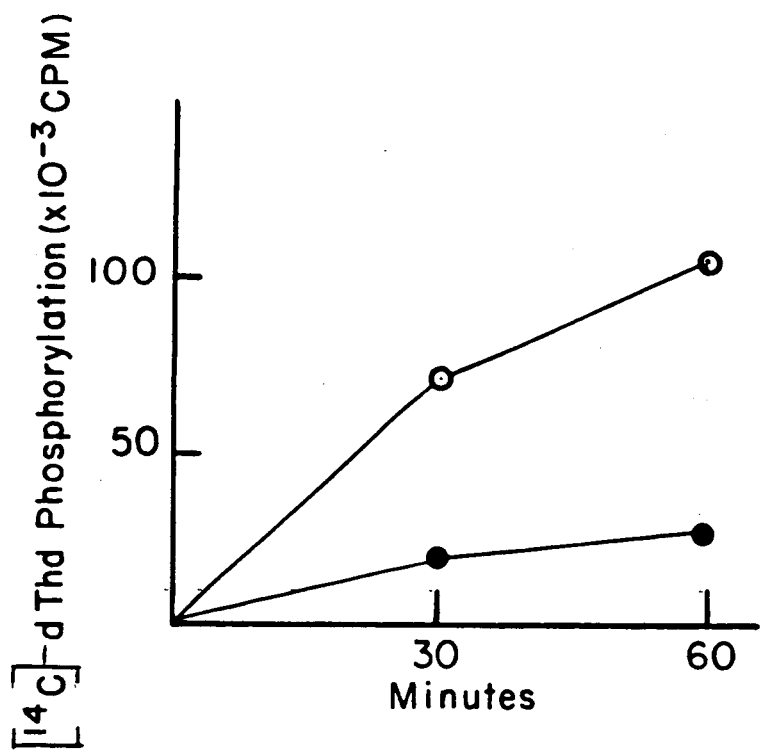
FIGS. 2C and 2D show the values obtained when HeLa S3 cells were used as the host cells for infection, (phosphorylation in the absence (O) or presence (●) of 25 μM 5'-Et-dThd).
Figure 2D:
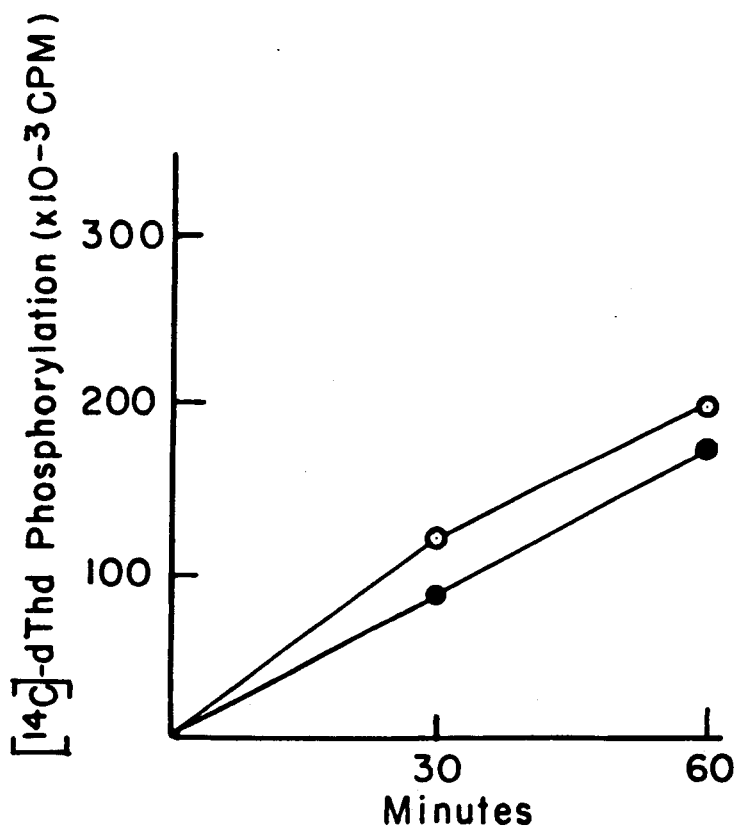

The role of host dThd kinase in virus-infected cells was explored by comparing the effect of 5'-Et-dThd (25 μM) on intracellular dThd phosphorylation in HeLa S3 and HeLa BU cells at 9 h post infection using the procedures described above. After a 1 h labeling period in the presence of drug, 12.5% and 80% of the untreated control dThd phosphorylating activities were present in HeLa BU cells infected with HSV-1 and HSV-2(see FIG. 2A and FIG. 2B, respectively; phosphorylation in the absence (0) or presence (●) of 25μM 5'-Et-dThd). When HeLa S3 cells were used as the host cells for infection, these values were increased to 25% and 88%, respectively (see FIG. 2C and 2D; phosphorylation in the absence (0) or presence (●) of 25 μM 5'-Et-dThd). Thus, the host dThd kinase activity in virus infected cells was still functional at 9 h post infection.

EXAMPLE 2

Activity of 5'-Et-dThd against dThd kinase activities induced by different types of strains of HSV Virus mutants that induce viral dThd kinases that exhibit altered substrate specificities (dThd kinase$^4$) and are resistant to selective antiviral agents have been isolated (see Larder, B. A., Derse, D. D., Y.-C. and Darby, G. (1983) J. Gen Viral 64:523–532). The effect of 5'-Et-dThd on the in vitro and intracellular dThd kinase activities of two such dThd kinase variants, Tr7 and B3 (ACV and BVDU resistant, respectively), were examined, together with their parental HSV-1 strain (SC16). The results are shown in Table I. The dThd kinase activities of these dThd kinase mutants, whose induced dThd kinase levels are similar to those of the parent SC16 strain, were sensitive to 5'-Et-dThd, with IC$_{50}$ values less than 10 μM both in vitro and in cell culture.

EXAMPLE 3

Effect of 5'-Et-dThd on dNTP pools in HSV-1 infected cells

In view of the potent inhibition of 5'-Et-dThd on HSV-1 dThd kinase and its associated dTMP kinase, the effect of 5'-Et-dThd on dNTP pools in HSV-1 infected cells was examined. At 12 h post infection, the dTTP pool of HeLa BU cells treated with 100 μM 5'-Et-dThd was reduced by 95% as compared to that of untreated infection control cells (FIG. 3A; HSV-1-infected HeLa BU cells (●,0) and HSV-1-infected HeLa S3 cells (▲, Δ) in the absence (solid symbols) or presence (open symbols) of 5'-Et-dThd). When HeLa S3 cells were used as the host cell for infection, the dTTP pool was reduced by 80% as compared to that of untreated infected control cells (FIG. 3A). This difference could be related to the activity of host dThd kinase in HeLa S3 cells.

When other dNTP pools in the virus infected cells were examined, no significant effect of 5'-Et-dThd were observed on dATP, dCTP and dGTP pools in 9 h HSV-1 (KOS)-infected HeLa BU cells was observed (FIG. 3B; the 100% values for dCTP (0) dGTP (Δ), dATP (X) and dTTP (●) pools in HSV-1-infected HeLa BU cells were 64, 65, 75 and 159 μM, respectively). Thus, it is unlikely that ribonucleotide reductase is inhibited by 5'-Et-dThd.

The decrease of dTTP pools in virus-infected cells caused by 5'-Et-dThd could be due to inhibition of viral dThd kinase or its intrinsic dTMP kinase activity. In order to explore whether inhibition of this intrinsic dTMP kinase activity (which constitutes 10% of the total dTMP kinase activity in 9 h infected cells) is sufficient to explain these results, the impact of 5'-Et-dThd on dTTP pools of HSV-1 (strain MDK)-infected HeLa BU cells was examined; the MDK strain of HSV-1 is unable to induce viral dThd kinase or its intrinsic dTMP kinase. At 100 $\mu$M 5'-Et-dThd, there was only 45% inhibition of dTTP pools (FIG. 3B; the dTTP pool of MDK-infected (□) HeLa BU cells was 70 $\mu$M). This suggested that the activity of host dTMP kinase in cells, even though partly inhibited by 5'-Et-DThd is sufficient to partially maintain the dTTP pool, and the inhibition of the viral dThd kinase-associated dTMP kinase is not a major factor in decreasing dTTP pools in 5'-Et-dThd treated cells.

EXAMPLE 4

Correlation of viral dThd kinase inhibition and dTTP pools

Figure 3:
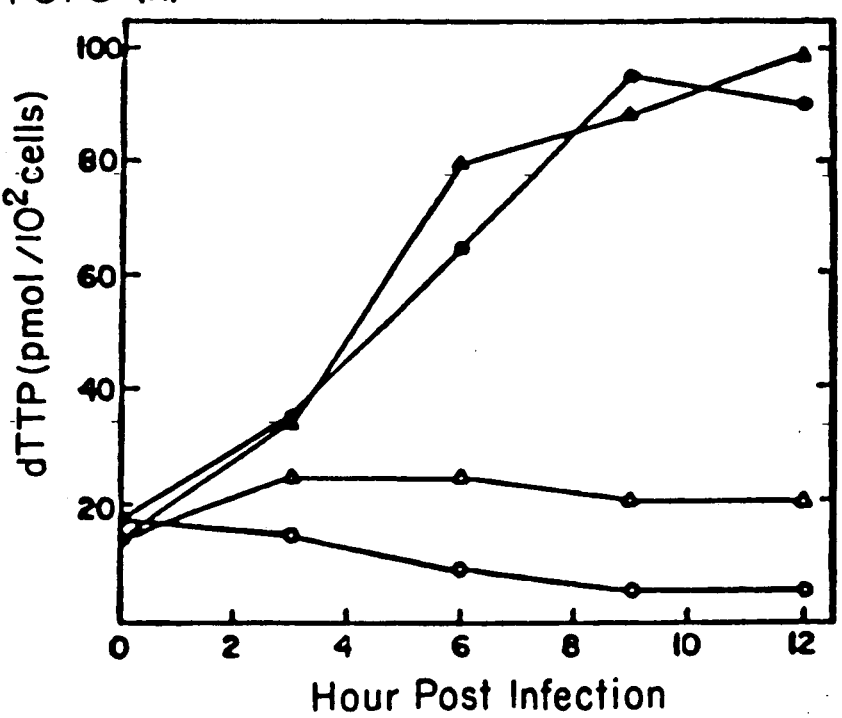
FIG. 3 Effect of 5'-Et-dThd on deoxynucleoside 5'-triphosphate (dNTP) pools in HSV-1-infected cells. HSV-1 infected HeLa BU cells (●,O) and HSV-1-infected HeLa S3 cells (▲,Δ) in the absence (solid symbols) or presence (open symbols) of 5'-Et-dThd.
Figure 3:
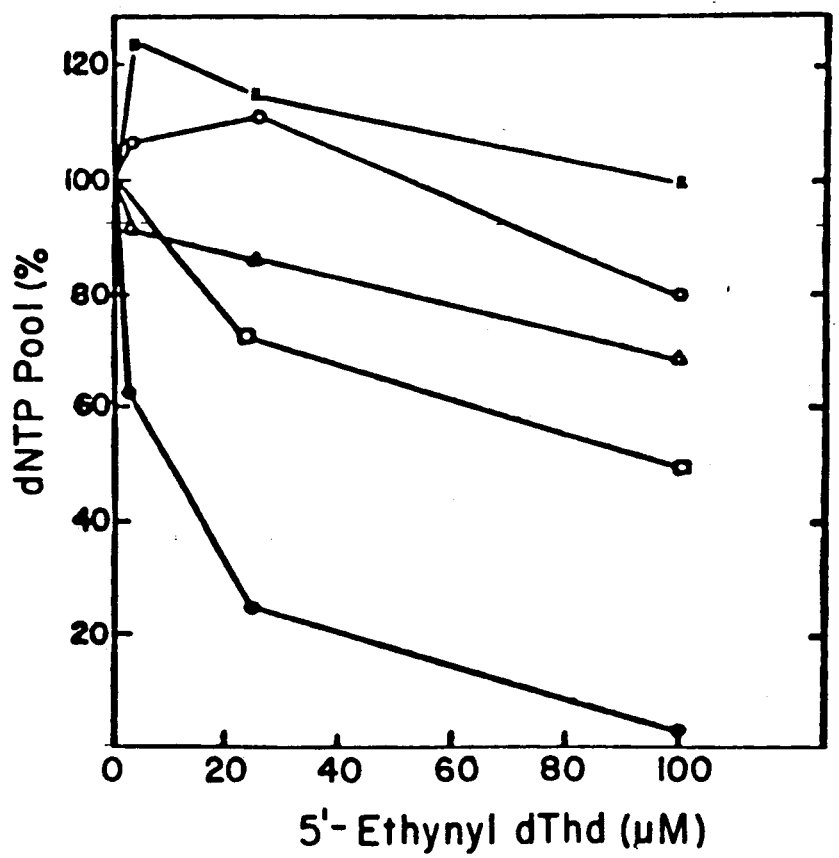

The impact of viral dThd kinase inhibition on dTTP pools in infected cells is demonstrated in FIG. 3 and suggests that viral dThd kinase activity is important for maintenance of this pool. This was investigated further by examining the correlation of viral dThd kinase activity with dTTP pool levels in HSV-1 (strain KOS)-infected cells (see FIG. 4). In this study, dThd kinase activity and dTTP pool levels were measured at 9 h post infection of HeLa S3 or HeLa BU cells with HSV-1 (KOS) in the presence of different concentrations of 5'-Et-dThd. A positive correlation was found between dThd kinase activity and dTTP levels in the infected cells. When the host dThd kinase activity contributed by HeLa S3 cells (15%) was subtracted from the total dThd kinase activity and replotted against the dTTP level (Δ), the result was superimposable on that obtained from dThd kinase-deficient infected cells (FIG. 4; all values are depicted as the % of the control dThd kinase activity and dTTP pool measurements in the absence of 5'-Et-dThd (100%); the concentrations of 5'-Et-dThd employed for studies with HSV-1 infected HeLa S3 cells were 0, 2.5, 25 and 100 $\mu$M, and those for HSV-1-infected HeLa BU cells were 0, 2, 10 and 100 $\mu$M; the 100% values for the dTTP pools in HSV-1 infected HeLa S3 and HeLa BU cells were 56 $\mu$M and 40 M, respectively; the 100% intracellular dThd kinase activity values for HSV-1- and HSV-2-infected HeLa BU cells were 90,000 and 50,000 cpm/$10^6$ cells, respectively). These results indicate that viral dThd kinase activity is of major importance in dTTP pool maintenance in HSV-1-infected cells.

EXAMPLE 5

Effects of 5'-Et-dThd on the antiviral activity of several agents

Figure 4:
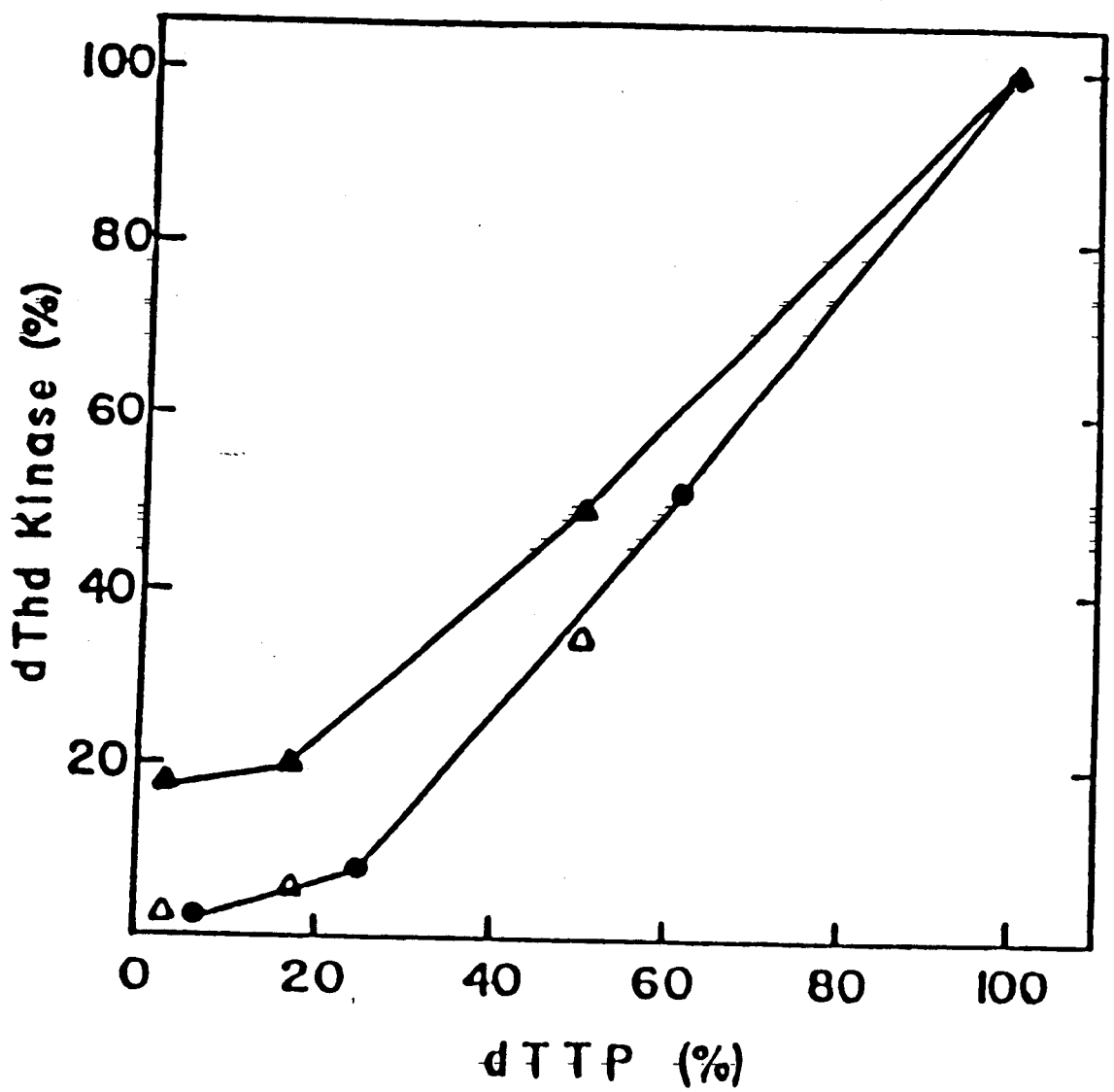
FIG. 4 Correlation of intracellular dThd kinase activity with dTTP pools. dThd kinase activity and dTTP pool levels were measured at 9 h post infection of HeLa S3 (▲) or HeLa BU (●) cells with HSV-1 (KOS) in the presence of different concentrations of 5'-Et-dThd. The host dThd kinase activity contributed by HeLa S3 cells (15%) was subtracted from the total dThd kinase activity and replotted against the dTTP level (Δ) (all values are depicted as the % of the control dThd kinase activity and dTTP pool measurements in the absence of 5'-Et-dThd (100%).

By itself, 5'-Et-dThd had no effect on virus yield (Table II) and on virus DNA synthesis as determined from isopycnic centrifugation studies where $^{32}PO_4$-labeled virus DNA was separated from host DNA. Nucleoside analogs have been developed based on the "selective alternate substrate" strategy, and depend on viral dThd kinase for their antiviral activity. The effect of 5'-Et-dThd on the antiviral efficacy of five such analogs, ACV, 9-(1, 3-dihydroxy-2-propoxymethyl) guanine (DHPG), fluoroido-arabinosyl-cytosine (FIAC), BVDU and 5'-amino-dThd (5'-NH$_2$-dThd) has been examined. The effect of 5'-Et-dThd on the activity of the five agents was determined by the virus yield assay using HSV-1 (strain KOS)-infected HeLa BU cells. At 100 $\mu$M, 5'-Et-dThd reversed the antiviral activity of ACV (15 $\mu$M), DHPG (2 $\mu$M), FIAC (1 $\mu$M), BVDU (1 $\mu$M) and 5'-NH$_2$-dThd (500 $\mu$M) 35-, 100-, 98-, 15- and 250-fold, respectively (Table II). The results indicate that virus dThd kinase is important for dTTP pool maintenance in infected cells (FIGS. 3 and 4). The results further indicate that the use of 5'-Et-dThd in the prophylaxis/prevention of virus reactivation would require a sequential order when used with virus dThd kinase-dependent antiviral agents.

Since 5'-Et-dThd significantly decreased the dTTP pools of infected cells, this compound was examined for its ability to enhance the antiviral activity of viral dThd kinase-independent agents that compete with dTTP for virus polymerase, for example, aphidicolin. HeLa BU cells infected with HSV-1 (KOS) were exposed to 0.2 $\mu$M aphidicolin both alone and together with varying concentrations of 5'-Et-dThd in a virus yield assay. The results (see Table III) indicate that the dThd analogue significantly enhanced the antiviral effect of aphidicolin. When cells were exposed to 100 $\mu$M 5'-Et-dThd together with aphidicolin, the % PFU observed was less than one half that observed when aphidicolin alone was used.

The foregoing invention has been described in some detail by way of examples for purposes of clarity and understanding. It will be obvious to those skilled in the art from a reading of the disclosure that it is contemplated that the method described herein will be used to inhibit the reactivation of HSV or herpes zoster virus in infected patients. It will also be obvious that it is contemplated that the method described herein will be used in combination with other antiviral programs to prevent establishment of the viral infection and to eliminate the virus from infected cells. Various changes in form and detail can be made without departing from the scope of the invention.

TABLE I

Effects of 5'-Et-dThd on Viral dThd kinase, virus dThd kinase-associated dTMP kinase, and host dTMP kinase activities[a]

| Virus type and strain | IC$_{50}$ of dThd kinase ($\mu$M) | | K$_i$[b] | IC$_{50}$ of virus-associated dTMP kinase ($\mu$M) | |
|---|---|---|---|---|---|
| | Intra-cellular[c] | In vitro[d] | | 25$\mu$M[e] | 100 $\mu$M[e] |
| HSV-1 | | | | | |
| KOS | 3 | 6 | 0.09 ± 0.02(49) | 0.3 | 0.8 |
| SC16 | 5 | 5 | | — | |
| Tr7 | 2 | 3 | | — | |
| B3 | 6 | 7 | | — | |
| HSV-2 | | | | | |
| 333 | 100 | 46 | 0.38 ± 0.18(23) | 60.0[f] | — |

[a] All studies were performed using HeLa BU cells.
[b] K$_i$ determinations were performed with affinity column-purified dThd kinase; numbers in parentheses reflect number of determinations for K$_i$ ± standard deviation.
[c] Intracellular [$^{14}$C]dThd phosphorylation.
[d] IC$_{50}$ determinations were performed with enzyme extracts of cells infected with designated virus; dThd concentration was 100 $\mu$M in the assay.
[e] dTMP substrate concentrations used in assay; crude extracts were used for assay.
[f] The activity of HSV-2 (333)-infected HeLa BU cells reflects host dTMP kinase activity.

TABLE II

Effect of 5'-Et-dThd on Activity of Antiviral Agents[a]

| Drug (μM) | % PFU with a 5'-Et-dThd conc. (μM) of: | | | |
| --- | --- | --- | --- | --- |
| | 0 | 2.5 | 25 | 100 |
| None | 100 | 97 | 96 | 99 |
| ACV(15) | 2 | 9 | 45 | 70 |
| FIAC(1) | 0.6 | 26 | 59 | |
| DHPG(2) | 0.1 | 0.2 | 4 | 10 |
| BVDU(1) | 0.9 | 9.5 | 13 | |
| 5'-NH$_2$-dThd(500) | 0.2 | 0.3 | 3 | 50 |

[a]The antiviral activities of several agents in the presence and absence of 5'-Et-dThd were determined using the virus yield assay with HSV-1(KOS) infected cells.

TABLE III

Effect of 5'-Et-dThd on Activity of Aphidicolin[a]

| Drug | %PFU with a 5'-Et-dThd conc. (μM) of: | | | |
| --- | --- | --- | --- | --- |
| | 0 | 5 | 20 | 100 |
| None | 100% | 100% | 100% | 100% |
| Aphidicolin (0.2 μM) | 54% | 65% | 45% | 21% |

[a]The antiviral activity of aphidicolin in the presence and absence of 5'-Et-dThd was determined using the the virus yield assay with HSV-1(KOS) infected cells.

What is claimed:

1. A method of selectively inhibiting herpes simplex virus-specified thymidine kinase comprising contacting mammalian cells infected with herpes simplex virus with an amount of 5'-ethynyl-thymidine sufficient to selectively inhibit said kinase.

2. A method as claimed in claim 1 wherein said herpes simplex virus is herpes simplex virus type 1.

3. A method as claimed in claim 1 wherein said herpes simplex virus is herpes simplex virus type 2.

4. A method as claimed in claim 1 wherein said herpes simplex virus is a variant resistant to acyclovir and/or (E)-5-(2-bromovinyl)-2-deoxyuridine.

5. A method of selectively inhibiting herpes zoster virus-specified thymidine kinase comprising contacting mammalian cells infected with herpes zoster virus with an amount of 5'-ethynyl-thymidine sufficient to selectively inhibit said kinase.

6. A method of reducing the thymidine 5'-triphosphate pool of mammalian cells infected with herpes simplex virus comprising contacting said infected cells with an amount of 5'-ethynylthymidine sufficient to reduce said pool.

7. A method according to claim 6 wherein said herpes simplex virus is herpes simplex virus type 1.

8. A method according to claim 6 wherein said herpes simplex virus is herpes simplex virus type 2.

9. A method of enhancing the antiviral activity of aphidicolin, comprising contacting mammalian cells infected with herpes simplex virus with an amount of 5'-ethynylthymidine sufficient to reduce the cellular pool of thymidine 5'-triphosphate together with an amount of aphidicolin sufficient to exert an antiviral effect.

10. A pharmaceutical composition comprising as an active ingredient an amount of 5'-ethynylthymidine sufficient to selectively inhibit herpes simplex or herpes zoster virus-specified thymidine kinase present in mammalian cells infected with said herpes simplex virus, together with a pharmaceutically acceptable carrier, which composition is in a form selected from the group consisting of a cream, lotion, tablet, capsule or sterile injectable solution.

11. A pharmaceutical composition according to claim 10 wherein said composition is in of a cream or lotion.

12. A pharmaceutical composition according to claim 10 wherein said composition is in the form of a tablet, capsule or sterile injectable solution.

13. A pharmaceutical composition as claimed in claim 10 wherein said herpes simplex virus is herpes simplex virus type 1.

14. A pharmaceutical composition as claimed in claim 10 wherein said herpes simplex virus is herpes simplex virus type 2.

* * * * *